(12) United States Patent
Kamakura

(10) Patent No.: US 10,760,892 B2
(45) Date of Patent: Sep. 1, 2020

(54) SENSOR

(71) Applicant: Seiko Epson Corporation, Tokyo (JP)

(72) Inventor: Tomoyuki Kamakura, Matsumoto (JP)

(73) Assignee: Seiko Epson Corporation (JP)

( * ) Notice: Subject to any disclaimer, the term of this patent is extended or adjusted under 35 U.S.C. 154(b) by 314 days.

(21) Appl. No.: 15/898,696

(22) Filed: Feb. 19, 2018

(65) Prior Publication Data
US 2018/0283844 A1    Oct. 4, 2018

(30) Foreign Application Priority Data

Mar. 30, 2017   (JP) .................................. 2017-069353

(51) Int. Cl.
| | |
|---|---|
| *G01B 7/00* | (2006.01) |
| *G01B 7/16* | (2006.01) |
| *H05K 1/02* | (2006.01) |
| *A61B 5/00* | (2006.01) |
| *G01L 1/22* | (2006.01) |
| *H05K 1/03* | (2006.01) |
| *H05K 3/28* | (2006.01) |

(52) U.S. Cl.
CPC .............. *G01B 7/18* (2013.01); *A61B 5/4528* (2013.01); *A61B 5/6833* (2013.01); *G01B 7/20* (2013.01); *G01L 1/2281* (2013.01); *H05K 1/028* (2013.01); *H05K 1/0283* (2013.01); *H05K 1/0393* (2013.01); *H05K 3/28* (2013.01); *H05K 2201/0129* (2013.01); *H05K 2201/0133* (2013.01); *H05K 2201/09263* (2013.01); *H05K 2201/09727* (2013.01); *H05K 2201/10151* (2013.01)

(58) Field of Classification Search
CPC ........... G01B 7/18; G01B 7/20; G01L 1/2268; G01L 1/2281
See application file for complete search history.

(56) References Cited

U.S. PATENT DOCUMENTS

| | | | | |
|---|---|---|---|---|
| 3,448,607 A | * | 6/1969 | Russell ................. | G01L 1/2281 73/766 |
| 5,375,474 A | * | 12/1994 | Moore, Sr. ............... | G01B 7/18 29/621.1 |
| 9,155,193 B2 | | 10/2015 | Kajiya et al. | |

(Continued)

FOREIGN PATENT DOCUMENTS

| | | | |
|---|---|---|---|
| DE | 2658324 A1 * | 6/1978 | ............. G01D 3/036 |
| JP | 2013-145842 A | 7/2013 | |

(Continued)

*Primary Examiner* — Blake A Tankersley
(74) *Attorney, Agent, or Firm* — Harness, Dickey & Pierce, P.L.C.

(57) ABSTRACT

A sensor includes a stretchable substrate having a stretching property, and a plurality of wires provided to the stretchable substrate, and the plurality of wires includes a first wire, and a second wire larger in resistance value variation due to extension of the stretchable substrate than the first wire. Further, the sensor includes a detection section adapted to correct a resistance value of the second wire in accordance with a resistance value of the first wire, and detect the extension of the stretchable substrate based on the resistance value of the second wire which has been corrected. Further, the detection section detects deterioration of the plurality of wires in accordance with the resistance value of the first wire.

9 Claims, 10 Drawing Sheets

(56) References Cited

U.S. PATENT DOCUMENTS

| | | | |
|---|---|---|---|
| 9,212,895 | B2 | 12/2015 | Suzuki et al. |
| 10,126,263 | B2 * | 11/2018 | Klootwijk .......... G01N 27/4146 |
| 2013/0056248 | A1 | 3/2013 | Kajiya et al. |
| 2013/0118267 | A1 | 5/2013 | Suzuki et al. |

FOREIGN PATENT DOCUMENTS

| | | |
|---|---|---|
| JP | 5284308 B2 | 9/2013 |
| JP | 5600030 B2 | 10/2014 |
| JP | 2015-055615 A | 3/2015 |
| JP | 5924725 B2 | 5/2016 |
| JP | 2016-143557 A | 8/2016 |

* cited by examiner

SENSOR

BACKGROUND

1. Technical Field

The present invention relates to a sensor.

2. Related Art

For example, in JP-A-2013-145842 (Document 1), there is disclosed a flexible circuit board having a stretchable circuit body having a stretchable insulating base material provided with a stretchable wiring section, and an unstretchable component mounting board to be stacked on a predetermined area of the stretchable circuit body. According to such a configuration, the wire becomes stretchable, and can preferably be used for a movable part of a robot or the like.

However, in the flexible circuit board of Document 1, by repeating a stretching action of the insulating base material, the resistance of the wiring section varies from an initial value. Therefore, in the case of applying the flexible circuit board of Document 1 to a motion sensor for detecting a motion of a human, a robot, or the like based on a variation in resistance value due to the stretching action of the wiring section, the action cannot be detected with high accuracy.

SUMMARY

An advantage of some aspects of the invention is to provide a sensor capable of detecting the variation in resistance value due to the stretching action of the wire with high accuracy.

The advantage described above can be achieved by the following configurations.

A sensor according to an aspect of the invention includes a stretchable substrate having a stretching property, and a plurality of wires provided to the stretchable substrate, wherein the plurality of wires includes a first wire, and a second wire larger in resistance value variation due to extension of the stretchable substrate than the first wire.

According to the aspect of the invention, it is possible to obtain the sensor capable of detecting the resistance value variation due to the extension and contraction of the wires with high accuracy.

In the sensor according to the aspect of the invention, it is preferable to further include a detection section adapted to correct a resistance value of the second wire in accordance with a resistance value of the first wire, and detect the extension and contraction of the stretchable substrate based on the resistance value of the second wire which has been corrected.

According to the aspect of the invention with this configuration, it is possible to detect the extension and contraction of the stretchable substrate in the sensor without outputting the resistance values of the first wire and the second wire to the outside. Therefore, the sensor high in convenience is obtained.

In the sensor according to the aspect of the invention, it is preferable that the detection section detects deterioration of the plurality of wires in accordance with the resistance value of the first wire.

According to the aspect of the invention with this configuration, it is possible for the sensor to prompt the user to replace the sensor itself, to replace or repair the wires, and so on. Therefore, it is prevented that the sensor degraded in detection accuracy continues to be used, and thus higher reliability can be exerted.

In the sensor according to the aspect of the invention, it is preferable that a variation in wiring length of the first wire with respect to the extension of the stretchable substrate is smaller than a variation in wiring length of the second wire.

According to the aspect of the invention with this configuration, it is possible to suppress the resistance value variation due to the extension and contraction of the stretchable substrate of the first wire to a low level.

In the sensor according to the aspect of the invention, it is preferable that the first wire extends and contracts together with the stretchable substrate with shape deformation, and the second wire extends and contracts together with the stretchable substrate with elastic deformation.

According to the aspect of the invention with this configuration, it is possible to detect the resistance value variation due to the factor other than the extension and contraction of the stretchable substrate using the first wire.

In the sensor according to the aspect of the invention, it is preferable that the first wire and the second wire are formed of the same material.

According to the aspect of the invention with this configuration, the variations of the first wire and the second wire in resistance value due to other factors than the extension and contraction of the stretchable substrate can be made equal to each other.

In the sensor according to the aspect of the invention, it is preferable that the first wire and the second wire are disposed side by side, and a separation distance between both end parts of the first wire and a separation distance between both end parts of the second wire are equal to each other.

According to the aspect of the invention with this configuration, the variation of the separation distance in the case in which the stretchable substrate extends or contracts can be made equal between the first wire and the second wire.

In the sensor according to the aspect of the invention, it is preferable that the plurality of wires includes a plurality of the second wires different in change rate of resistance with respect to the extension of the stretchable substrate from each other.

According to the aspect of the invention with this configuration, the extension and contraction of the stretchable substrate can be detected based on the resistance value variations of the plurality of second wires, and therefore, the extension and contraction of the stretchable substrate can accurately be detected compared to the case in which, for example, the number of the second wires is one.

In the sensor according to the aspect of the invention, it is preferable that the second wires are different in length from each other.

According to the aspect of the invention with this configuration, the resistance value variations of the second wires with respect to the extension of the stretchable substrate can be made different from each other with a simple configuration.

In the sensor according to the aspect of the invention, it is preferable that the second wires are different in cross-sectional area from each other.

According to the aspect of the invention with this configuration, the resistance value variations of the second wires with respect to the extension of the stretchable substrate can be made different from each other with a simple configuration.

BRIEF DESCRIPTION OF THE DRAWINGS

The invention will be described with reference to the accompanying drawings, wherein like numbers reference like elements.

DESCRIPTION OF EXEMPLARY EMBODIMENTS

The sensor according to the invention will hereinafter be described in detail based on some preferred embodiments shown in the accompanying drawings.

First Embodiment

Figure 1:
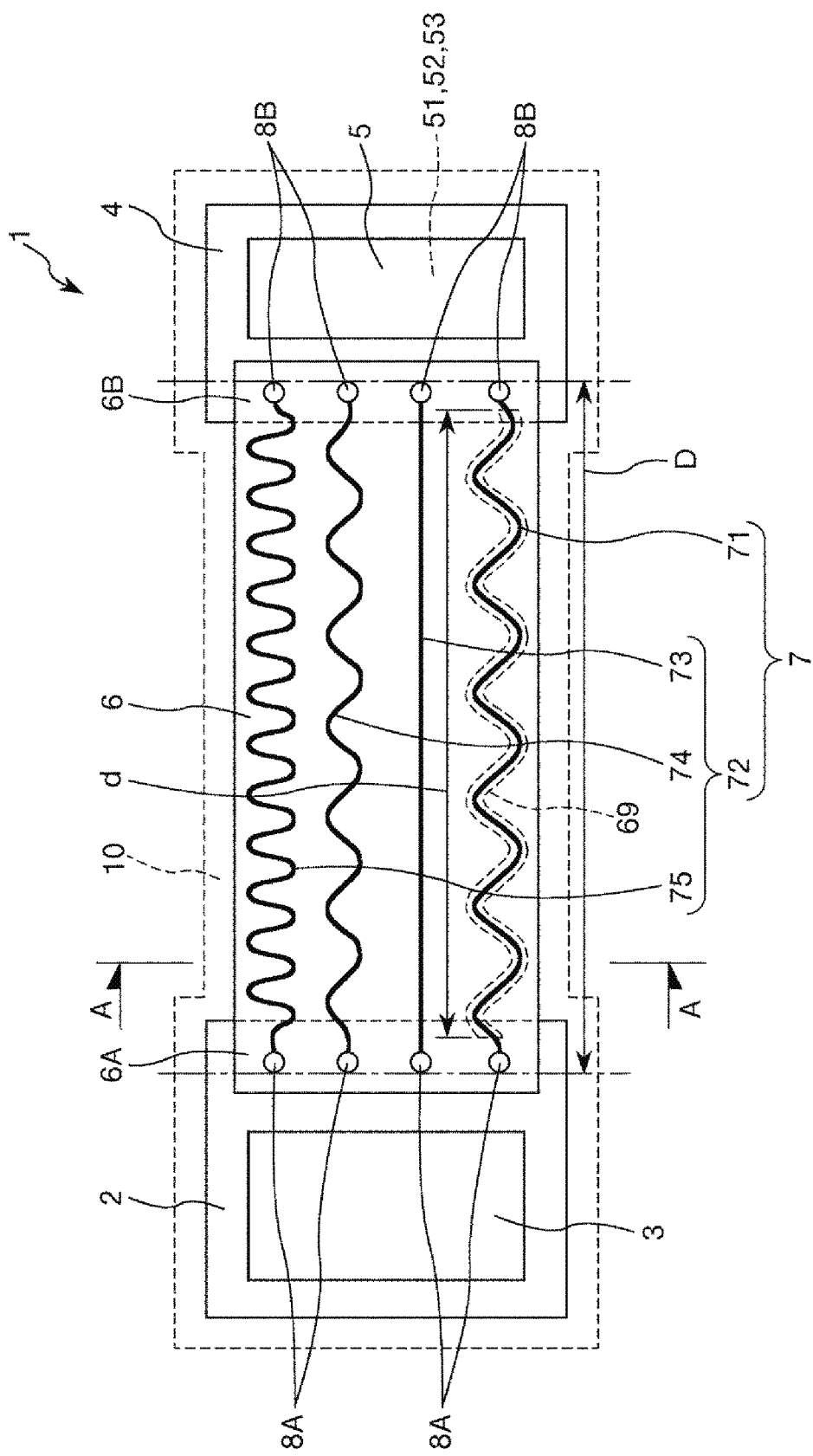
FIG. 1 is a plan view showing a sensor according to a first embodiment of the invention.
Figure 2:
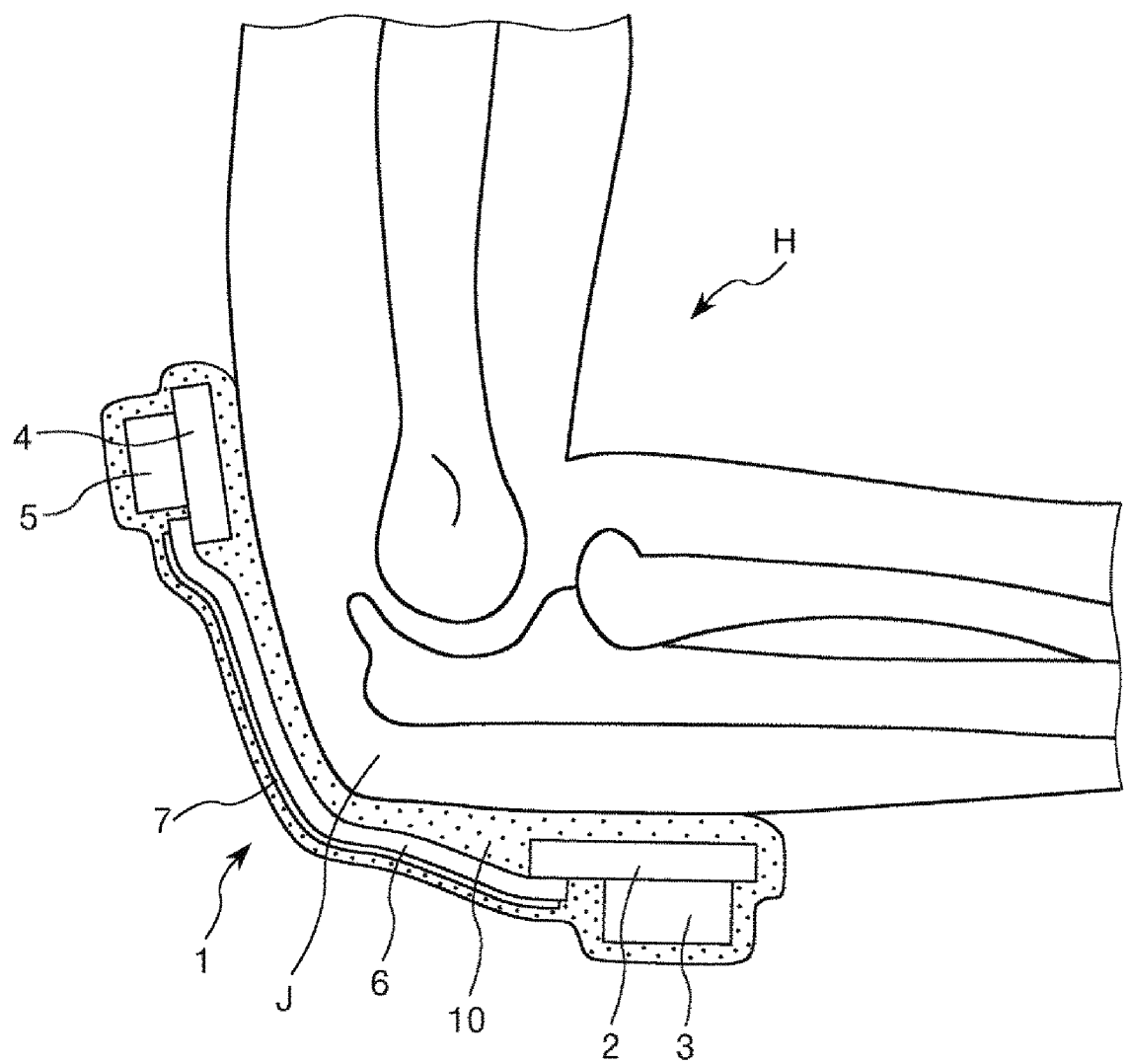
FIG. 2 is a diagram showing a mounting state of the sensor shown in FIG. 1.
Figure 3:
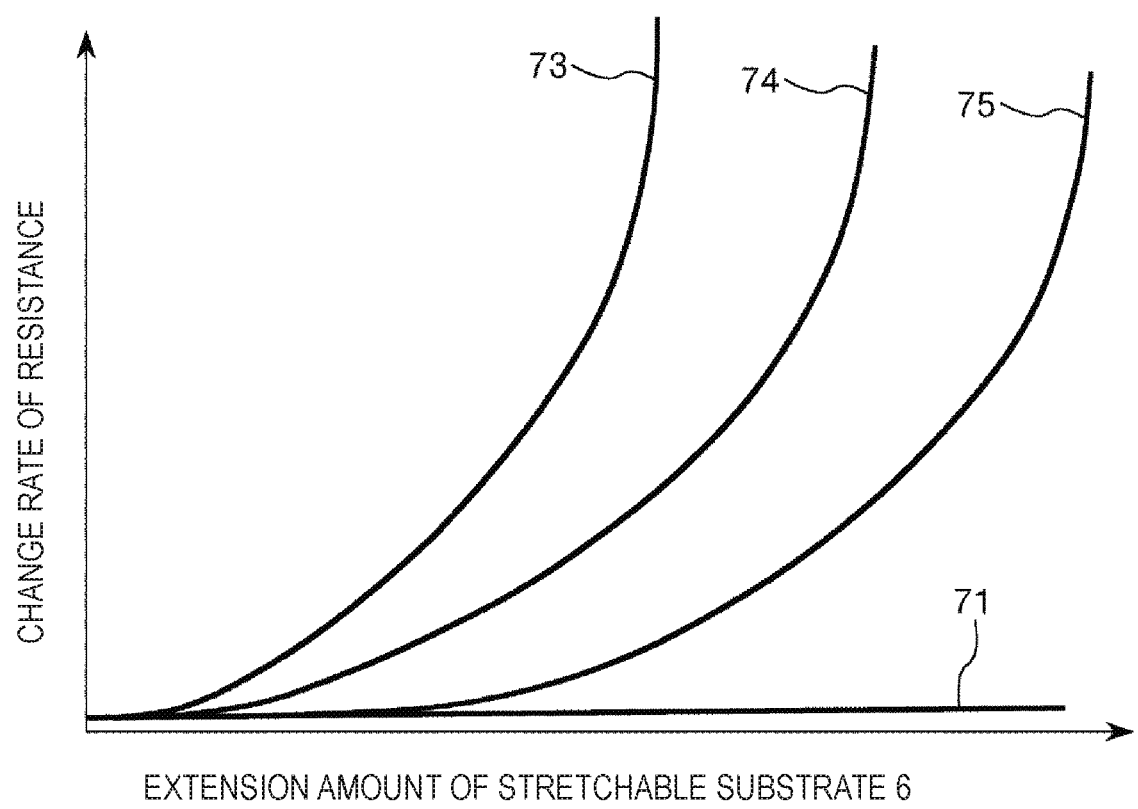
FIG. 3 is a graph showing a relationship between an extension amount and a change rate of the resistance of each of sensing wires.
Figure 4:
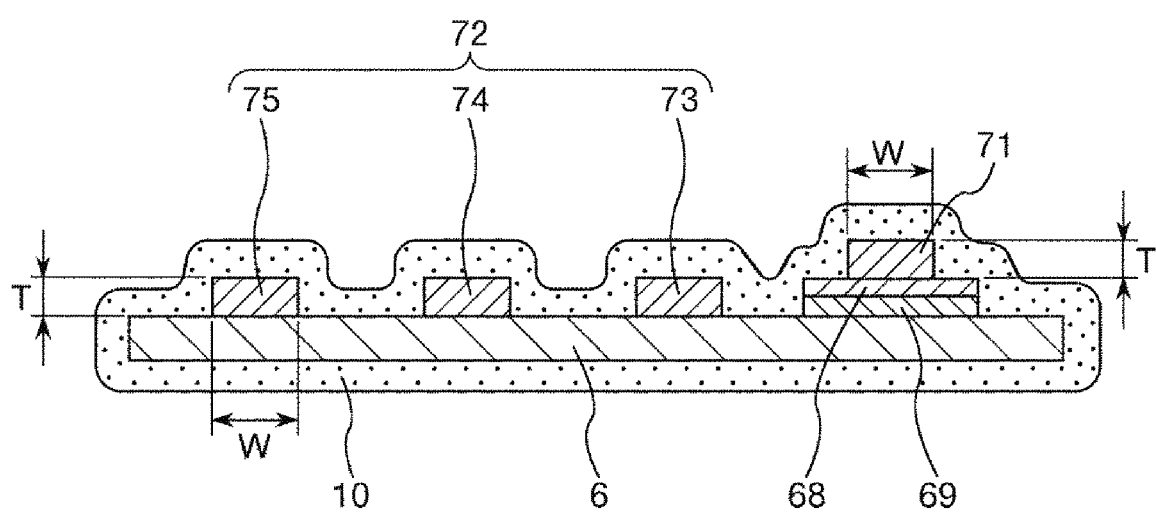
FIG. 4 is a cross-sectional view along the line A-A in FIG. 1.

FIG. 1 is a plan view showing the sensor according to a first embodiment of the invention. FIG. 2 is a diagram showing a mounting state of the sensor shown in FIG. 1. FIG. 3 is a graph showing a relationship between an extension amount and a change rate of the resistance of each of sensing wires. FIG. 4 is a cross-sectional view along the line A-A in FIG. 1.

The sensor 1 shown in FIG. 1 is a wearable terminal used while mounted on a movable body, and available as a motion sensor for detecting a motion of the movable body. It should be noted that the movable body is not particularly limited, but there can be cited, for example, a variety of kinds of animals including humans, a variety of types of robots including joints, and a variety of moving bodies such as a vehicle and an airplane. It should be noted that in the present embodiment, for the sake of convenience of explanation, as shown in FIG. 2, the description will be presented citing the case in which the movable body is a human H and the sensor 1 is disposed on the arm so as to straddle a joint J in the elbow, as an example.

As shown in FIG. 1, the sensor 1 has a first substrate 2, a motion detection section 3 (a detection section) provided to the first substrate 2, a second substrate 4, a functional section 5 provided to the second substrate 4, a stretchable substrate 6 located between the first substrate 2 and the second substrate 4 for connecting these constituents, wires 7 provided to the stretchable substrate 6, and a coating section 10 for covering these constituents. As shown in FIG. 2, the sensor 1 is mounted on a skin of the human H so that the stretchable substrate 6 straddles the joint J, the first substrate 2 is fixed to the upper arm, and the second substrate 4 is fixed to the forearm. Thus, the wires 7 extend and contract together with the stretchable substrate 6 based on bending and stretching of the joint J, and the resistance value of each of the wires 7 varies in accordance with the stretching degree. Further, based on the variation in the resistance value of each of the wires 7, the motion detection section 3 detects the stretch and contract of the stretchable substrate 6. Thus, the bending and stretching of the joint J can be detected. Such a sensor 1 will hereinafter be described in detail.

The first substrate 2 and the second substrate 4 are each formed of a hard rigid board. Such first substrate 2 and second substrate 4 are not particularly limited, but there can be used, for example, a glass epoxy board used for the print wiring board, a glass composite board, and a ceramics board. It should be noted that the first substrate 2 and the second substrate 4 each can also be formed of a flexible board having flexibility.

As described above, the stretchable substrate 6 is a region to be bonded to the place the motion of which needs to be detected such as a joint. Such a stretchable substrate 6 has a stretching property, and by extension, flexibility, and is therefore deformable along the surface of the skin of the human H when mounted thereon, and is further stretchable in accordance with the motion of the joint J. Further, the stretchable substrate 6 has an elongated shape elongated in the stretching direction (the direction in which the first substrate 2 and the second substrate 4 align), and one of the end parts of the stretchable substrate 6 forms a first fixation section 6A connected and fixed to the first substrate 2, and the other of the end parts thereof forms a second fixation section 6B connected and fixed to the second substrate 4. It should be noted that the shape of the stretchable substrate 6 is not particularly limited.

The constituent material of such a stretchable substrate 6 is not particularly limited providing the material has a stretching property, and there can be used, for example, a variety of types of thermoplastic elastomer such as polyurethane elastomer, styrene thermoplastic elastomer, olefinic thermoplastic elastomer, vinyl chloride thermoplastic elastomer, esters thermoplastic elastomer, amide thermoplastic elastomer, silicone thermoplastic elastomer, and fluorinated thermoplastic elastomer, and a variety of rubber materials such as acrylic rubber, silicone rubber, butadiene rubber, and styrene rubber. Further, the stretchable substrate 6 can also be a stacked body having two or more layers stacked on one another. In this case, there can be cited what is obtained by stacking layers of respective materials different from each other selected from the materials described above.

As shown in FIG. 1, the stretchable substrate 6 is provided with the wires 7. The wires 7 include a reference wire 71 (a reference wire) as a first wire, and sensing wires 72 (detection wires) as second wires. Further, the sensing wires 72 include a first sensing wire 73, a second sensing wire 74, and a third sensing wire 75 different in wiring length from each other. The reference wire 71, the first sensing wire 73, the second sensing wire 74, and the third sensing wire 75 are arranged side by side in a width direction (a vertical direction in FIG. 1) of the stretchable substrate 6, and are each disposed along a stretching direction (a longitudinal direction; a lateral direction in FIG. 1) of the stretchable substrate 6. It should be noted that it is required to dispose at least one sensing wire 72, and it is also possible to, for example, omit one or two of the first, second, and third sensing wires 73, 74, 75. Further, the number of the sensing wires 72 can also be four or more.

Further, although not shown in the drawings, on the stretchable substrate 6, there is disposed an insulating coating layer so as to cover the wires 7, wherein the insulating coating layer has an equivalent stretching property to the stretchable substrate 6, and protects the wires 7, and at the same time prevents breaking and shorting of the wires.

Further, the wires 71, 73, 74, 75 have substantially the same cross-sectional shapes. It should be noted that the cross-sectional shapes of the wires 71, 73, 74, 75 are each a rectangular shape in the present embodiment, but are not particularly limited, and each can also be, for example, a circular shape, an elliptical shape, or a semicircular shape. Further, it is also possible for at least one of the wires 71, 73, 74, 75 to be different in cross-sectional shape from the rest of the wires.

Further, the wires 71, 73, 74, 75 each have a configuration having a stretching property, extending and contracting in accordance with the extension and contraction of the stretchable substrate 6, and not being broken due to the extension of the stretchable substrate 6. Further, the constituent material of the wires 71, 73, 74, 75 is not particularly limited, but a material obtained by adding a conductive material to a polymer having a stretching property (elasticity) is preferable. As the polymer having a stretching property, there can be cited, for example, a variety of types of thermoplastic elastomer such as polyurethane elastomer, styrene thermoplastic elastomer, olefinic thermoplastic elastomer, vinyl chloride thermoplastic elastomer, esters thermoplastic elastomer, amide thermoplastic elastomer, silicone thermoplastic elastomer, and fluorinated thermoplastic elastomer, and a variety of rubber materials such as acrylic rubber, silicone rubber, butadiene rubber, and styrene rubber. As the conductive material, there can be cited a variety of types of fillers and a variety of types of polymers of, for example, metal (e.g., Au, Ag, Cu, Ni, Zn, and Al), metal oxides (e.g., Sb-doped $SnO_2$, Sn-doped $In_2O_3$, and Al-doped ZnO), and carbons (e.g., conductive carbon black and graphite). Further, it is also possible to add cellulose nanofibers, carbon nanofibers, or the like to the materials described above, and in such a case, a reinforcement effect of the wires is exerted in addition to the improvement in conductivity, and the wires 71, 73, 74, 75 hard to be broken can be obtained.

Further, as shown in FIG. 1, the four wires 71, 73, 74, 75 are equal to each other in separation distance D between the both ends. It should be noted that the concept of "equal to each other in separation distance D" is a concept including the case in which a minute error (e.g., an error within a range of about ±5% of the separation distance D) which can inevitably occur in the manufacturing process occurs in the separation distances D thereof in addition to the case in which the separation distances D thereof completely coincide with each other.

Further, one end parts of the wires 71, 73, 74, 75 each constitute a terminal 8A located in the first fixation section 6A, and are each electrically connected to the motion detection section 3 via the terminal 8A. Further, the other end parts of the wires 71, 73, 74, 75 each constitute a terminal 8B located in the second fixation section 6B, and are each electrically connected to the functional section 5 via the terminal 8B.

The first fixation section 6A is fixed to the first substrate 2, and is therefore restricted in extension and contraction thereof. Therefore, by disposing the terminals 8A of the respective wires 71, 73, 74, 75 in the first fixation section 6A, it is prevented that tensile stress acts on the terminals 8A due to the extension and contraction of the stretchable substrate 6 to cause breaking wire in the terminals 8A, and thus, it is possible to keep the connection state between the wires 71, 73, 74, 75 and the motion detection section 3 in good condition. Similarly, the second fixation section 6B is fixed to the second substrate 4, and is therefore restricted in extension and contraction thereof. Therefore, by disposing the terminals 8B of the respective wires 71, 73, 74, 75 in the second fixation section 6B, it is prevented that tensile stress acts on the terminals 8B due to the extension and contraction of the stretchable substrate 6 to cause breaking wire in the terminals 8B, and thus, it is possible to keep the connection state between the wires 71, 73, 74, 75 and the functional section 5 in good condition.

Further, as shown in FIG. 1, the reference wire 71 has a meandering shape (a wave shape), and has wiring length (the separation distance between the both ends in the case of being stretched to have a linear shape) longer than the separation distance D. Further, the first sensing wire 73 has a linear shape to have wiring length roughly equal to the separation distance D. Further, the second sensing wire 74 has a meandering shape, and has wiring length longer than the separation distance D, and longer than that of the first sensing wire 73. Further, the third sensing wire 75 has a meandering shape, and has wiring length longer than the separation distance D, and longer than that of the second sensing wire 74. It should be noted that the shape of the reference wire 71 is not particularly limited providing the wiring length is longer than the separation distance D, and can also be, for example, a triangular wave shape, or a spiral shape. Further, the shapes of the first, second, and third sensing wires 73, 74, 75 are also not particularly limited as long as the relationship of the wiring length described above is maintained.

Further, the reference wire 71 and the first, second, and third sensing wires 73, 74, 75 are each designed so that the resistance values in the natural state become equal to each other. Thus, it is possible to more accurately perform a correction by the motion detection section 3 described later. It should be noted that the concept that "the resistance values are equal to each other" is a concept including the case of including a minute error inevitably occurs in the manufacturing process in addition to the case in which the resistance values completely coincide with each other. It should be noted that it is possible for at least one of the reference wire 71 and the first, second, and third sensing wires 73, 74, 75 to be different in resistance value from the rest of the wires.

The reference wire 71 is a wire in which no substantial elastic deformation (a change in wiring length or cross-sectional area) occurs even if the stretchable substrate 6 extends or contracts, and a substantial shape deformation (e.g., a deformation in which the meandering shape is stretched to be a linear shape, and which is accompanied by no substantial elastic deformation) occurs due to the extension and contraction of the stretchable substrate 6. In contrast, the sensing wires 72 (the first, second, and third sensing wires 73, 74, 75) are wires in which if the extension or contraction occurs in the stretchable substrate 6, an elastic deformation (a change in wiring length or cross-sectional area) corresponding to the extension or contraction of the stretchable substrate 6.

Since the reference wire 71 follows the extension and contraction of the stretchable substrate 6 while keeping the wiring length and the cross-sectional area (width W×thickness T) substantially constant, the resistance value of the reference wire 71 does not substantially change due to the extension and contraction of the stretchable substrate 6. In contrast, since the sensing wires 72 (the first, second, and third sensing wires 73, 74, 75) follows the extension and contraction of the stretchable substrate 6 while changing the wiring length and the cross-sectional area (width W×thickness T), the resistance values change (the resistance value rises when the stretchable substrate 6 extends, and the resistance value falls when the stretchable substrate 6 contracts on the contrary) due to the extension and contraction of the stretchable substrate 6.

Therefore, the sensing wires 72 are larger in resistance value variation due to the extension and contraction of the stretchable substrate 6 than the reference wire 71. The resistance value of the reference wire 71 does not change due to the extension and contraction of the stretchable substrate 6 in the present embodiment, but can change, and in this case, it is sufficient for the resistance value variation of the reference wire 71 to be smaller than the resistance value variation of the sensing wires 72 in the case of extending the stretchable substrate 6 from the natural state (the state in which external force is not substantially applied) as much as a predetermined length. Specifically, defining the resistance value in the natural state of the stretchable substrate 6 as $\Omega 1$, and the resistance value in the state in which the stretchable substrate 6 extends as much as a predetermined length as $\Omega 2$, the resistance value variation $\Delta\Omega 71$ ($\Omega 1-\Omega 2$) of the reference wire 71 is preferably no higher than 1/10 of the resistance value variation $\Delta\Omega 72$ ($\Omega 1-\Omega 2$) of the sensing wires 72, more preferably no higher than 1/15 thereof, and further more preferably no higher than 1/20 thereof. Thus, it is possible to suppress the resistance value variation due to the extension and contraction of the stretchable substrate 6 of the sensing wires 72 to a sufficiently low level.

It should be noted that as described above, the first, second, and third sensing wires 73, 74, 75 are different in wiring length from each other. Therefore, as shown in FIG. 3, the resistance value variations (change rates of the resistances) occurring when the stretchable substrate 6 extends or contracts are different from each other. More specifically, the first sensing wire 73 is the shortest in wiring length of the three wires 73, 74, 75, and is the largest in variation of the wiring length occurring when the stretchable substrate 6 extends or contracts, and therefore becomes the highest in change rate of the resistance. In contrast, the third sensing wire 75 is the longest in wiring length of the three wires 73, 74, 75, and is the smallest in variation of the wiring length occurring when the stretchable substrate 6 extends or contracts, and therefore becomes the lowest in change rate of the resistance. Further, the second sensing wire 74 has the resistance value variation intermediate between those of the first sensing wire 73 and the third sensing wire 75.

Among the reference wire 71 and the sensing wires 72 described above, the sensing wires 72 (the first, second, and third sensing wires 73, 74, 75) are wires for detecting the extension and contraction of the stretchable substrate 6 based on the resistance value variations due to the extension and contraction (the elastic deformation). However, since the resistance values of the sensing wires 72 also vary due to factors (e.g., environmental temperature, environmental moisture, and deterioration with time) other than the extension and contraction of the stretchable substrate 6, it is unachievable to accurately detect the extension and contraction of the stretchable substrate 6 based on the resistance value variations of the sensing wires 72, and the accuracy also declines over time.

Therefore, in the sensor 1, there is provided the reference wire 71 for detecting (referring to) the resistance value variation due to the factors (e.g., the deterioration with time) other than the extension and contraction of the stretchable substrate 6. Since the reference wire 71 does not change in resistance value due to the extension and contraction of the stretchable substrate 6, the resistance value variation of the reference wire 71 can be assumed as the resistance value variation due to the factors other than the extension and contraction of the stretchable substrate 6. Therefore, by correcting the resistance values of the sensing wires 72 based on the resistance value of the reference wire 71, it is possible for the motion detection section 3 to cancel the resistance value variations due to the factors other than the extension and contraction of the stretchable substrate 6, and thus, more accurately detect the extension and contraction of the stretchable substrate 6, namely a motion of the human H.

It should be noted that in the present embodiment, in the case in which, for example, the resistance value in the state in which no external stress due to bending or stretching of the joint J or the like is applied is defined as R, and the resistance value in the state in which external stress is applied to extend the stretchable substrate 6 is defined as R' in the wires (the sensing wires 72 and the reference wire 71), the resistance value variation is defined as the change rate of the resistance represented by R/R'. The invention is not limited to this configuration, and the resistance value variation can also be defined as a change amount of the resistance represented by R-R'.

The reference wire 71 and the sensing wires 72 (the first, second, and third sensing wires 73, 74, 75) are formed of substantially the same materials. Thus, the variations (conditions) of the reference wire 71 and the sensing wires 72 in resistance value due to the factors other than the extension and contraction of the stretchable substrate 6 can be made equal to each other. Therefore, it is possible to more accurately correct the resistance values of the sensing wires (i.e., cancel the resistance value variation due to the factors other than the extension and contraction of the stretchable substrate 6) based on the resistance value of the reference wire 71. It should be noted that the concept of the "same material" described above is a concept including the case of including a minute error inevitably occurring in the manufacturing process such as the case in which the contents of the components are slightly different from each other, or the case in which a small amount of material not included in one of the materials is included in the other of the materials, in addition to the case in which the materials completely coincide with each other. It should be noted that the reference wire 71 and the sensing wires 72 are not required to be formed of the same material, and can also be formed of respective materials different from each other.

Further, as described above, the reference wire 71 and the sensing wires 72 (the first, second, and third sensing wires 73, 74, 75) are equal in separation distance D to each other. Thus, the deformation amounts (the variation of the separation distance D) of the reference wire 71 and the sensing wires 72 due to the extension and contraction of the stretchable substrate 6 can be made substantially equal to each other. Therefore, it is possible to suppress the dissociation of the deterioration degree between the wires 71, 72 due to the repetition of the extension and contraction. Therefore, it is possible to maintain the detection accuracy at a high level for a long period of time.

Here, in order to make the reference wire 71 become a wire in which no elastic deformation (the change in wiring length and the cross-sectional area) occurs when the stretchable substrate 6 extends or contracts, and the substantial shape deformation (the change in pitch and amplitude of the wave shape) occurs due to the extension and contraction of the stretchable substrate 6, the stretchable substrate 6 is provided with a restriction section 69 for restricting (suppressing) the extension and contraction due to the elastic deformation of the reference wire 71 as shown in FIG. 1 and FIG. 4.

As shown in FIG. 4, the restriction section 69 has a film-like shape, and is disposed between the stretchable substrate 6 and the reference wire 71. Specifically, the restriction section 69 is disposed so as to overlap the reference wire 71 in a planar view of the stretchable substrate 6. The restriction section 69 is poorer in stretching property than the stretchable substrate 6, and substantially has no stretching property in particular in the present embodiment. Further, as shown in FIG. 1, the restriction section 69 has total length longer than the separation distance D between the both ends. In particular in the present embodiment, the restriction section 69 has a meandering shape (a wave shape) corresponding to the shape of the reference wire 71, and is disposed so as to extend along the reference wire 71 in the longitudinal direction of the stretchable substrate 6.

Such a restriction section 69 does not follow the extension and contraction of the stretchable substrate 6 due to the elastic deformation, but follows the extension and contraction of the stretchable substrate 6 due to the shape deformation (the change in pitch and amplitude of the wave shape). Therefore, as a result, the reference wire 71 located on the restriction section 69 also makes substantially the same deformation as that of the restriction section 69, and becomes not to follow the extension and contraction of the stretchable substrate 6 due to the elastic deformation, but to follow the extension and contraction of the stretchable substrate 6 due to the shape deformation. As described above, by disposing the restriction section 69, it is possible to easily and surely suppress the elastic deformation of the reference wire 71.

It should be noted that the constituent material of the restriction section 69 is not particularly limited, and there can be used, for example, a variety of types of metal such as iron, nickel, cobalt, gold, silver, copper, manganese, aluminum, and magnesium, or an alloy including at least one of these materials. Thus, there can be obtained the restriction section 69 harder to elastically be deformed. Further, it is advantageous to form the restriction section with a metal material from a viewpoint that the restriction section 69 can also be used as electrical wiring. It should be noted that in the present embodiment, as shown in FIG. 4, in order to isolate the restriction section 69 and the reference wire 71 from each other, an interlayer insulating film 68 is disposed between these constituents. It should be noted that the isolation method between the restriction section 69 and the reference wire 71 is not particularly limited, but it is also possible to, for example, dispose the reference wire 71 on a surface located on one side of the stretchable substrate 6, and the restriction section 69 on a surface located on the other side thereof, to thereby isolate these constituents using the stretchable substrate 6.

The motion detection section 3 detects the stretching degree (stretching amount) of the stretchable substrate 6 based on the resistance value variations of the reference wire 71 and the sensing wires 72, and further detects the motion of the joint J based on the stretching amount of the stretchable substrate 6.

According to the specific description of the detection method, for example, the motion detection section 3 detects the resistance values of the first, second, and third sensing wires 73, 74, 75 and the resistance value of the reference wire 71 in real time, and then corrects each of the resistance values of the first, second, and third sensing wires 73, 74, 75 based on the resistance value of the reference wire 71. It should be noted that the resistance values of the respective wires 71, 73, 74, 75 can be detected from the voltage between the both ends and the current of each of the wires 71, 73, 74, 75.

Specifically, for example, the resistance value of the reference wire 71 or a value obtained by multiplying the resistance value by a predetermined coefficient (which can differs between the wires 73, 74, 75) is subtracted from the resistance values of the first, second, and third sensing wires 73, 74, 75. Then, the motion detection section 3 detects the stretching amount of the stretchable substrate 6 based on the resistance values of the first, second, and third sensing wires 73, 74, 75 having been corrected.

The detection method of the stretching amount of the stretchable substrate 6 is not particularly limited, but there can be cited, for example, a method of obtaining in advance an average value of the resistance values thus corrected of the first, second, and third sensing wires 73, 74, 75 in a reference state (e.g., a stretching state in the state in which the joint J is in a stretched state) of the stretchable substrate 6, storing the average value as a reference value, and then comparing the reference value with an average value of the resistance values having been corrected of the first, second, and third sensing wires 73, 74, 75 detected in real time to thereby detect the stretching amount from the reference state of the stretchable substrate 6. Further, as a different method from this method, there can be cited a method of, for example, obtaining in advance a median value of the resistance values thus corrected of the first sensing wire 73 and the third sensing wire 75 in the reference state of the stretchable substrate 6, storing the median value as a reference value, and comparing the reference value with the median value of the resistance values thus corrected of the first sensing wire 73 and the third sensing wire 75 in real time to thereby detect the stretching amount from the reference state of the stretchable substrate 6.

Further, it is also possible to adopt a configuration in which, for example, the stretching amount of the stretchable substrate 6 is detected based on the resistance value thus corrected of the first sensing wire 73 in the case in which the stretching amount of the stretchable substrate 6 is small, the stretching amount of the stretchable substrate 6 is detected based on the resistance value thus corrected of the second sensing wire 74 in the case in which the stretching amount of the stretchable substrate 6 is larger than the above, and the stretching amount of the stretchable substrate 6 is detected based on the resistance value thus corrected of the third sensing wire 75 in the case in which the stretching amount of the stretchable substrate 6 is still larger than the above. In other words, it is possible to change the wire to be used for the detection in accordance with the stretching degree of the stretchable substrate 6.

The motion detection section 3 has a function of detecting the deterioration of the wires 7 in addition to the function of detecting the extension and contraction of the stretchable substrate 6 described above. The wires 7 deteriorate with time due to the repetitive extension and contraction and so on. If the wires 7 excessively deteriorate, even if the correction using the resistance value of the reference wire 71 is performed, there is a possibility that the extension and contraction of the stretchable substrate 6 cannot accurately be detected. Therefore, the motion detection section 3 is configured so as to be able to detect the deterioration of the wires 7 to determine whether or not the sensor 1 is in a condition of being capable of accurately detecting the extension and contraction (the motion of the human H) of the stretchable substrate 6. Thus, it is possible for the sensor 1 to prompt the user to replace the sensor 1 itself, to replace or repair the wires 7, and so on. Therefore, it is prevented that the sensor 1 degraded in detection accuracy continues to be used, and thus higher reliability can be exerted.

The method by the motion detection section 3 to detect the deterioration of the wires 7 is not particularly limited, but in the present embodiment, there is adopted a configuration in which the motion detection section 3 makes the determination based on the resistance value of the reference wire 71. Specifically, there can be cited a method of determining an upper limit of the resistance value of the reference wire 71 in advance, then storing the upper limit value as a threshold value, then determining that "the wires 7 are not deteriorated" if the present resistance value of the reference wire 71 is equal to or lower than the threshold value, and determining that "the wires 7 are deteriorated" if the present resistance value thereof exceeds the threshold value. According to such a method, it is possible to detect the deterioration of the wires 7 with a relatively simple configuration. It should be noted that the motion detection section 3 can also be provided with an annunciation section for announcing the fact that the wires 7 are deteriorated with, for example, light, sounds, or vibrations.

The functional section 5 has, for example, a storage section 51 for storing the result detected by the motion detection section 3, a communication section 52 for outputting the result detected by the motion detection section 3 to the outside, and a battery 53 acting as a power supply for the sensor 1. The functional section 5 having such a configuration is electrically connected to the motion detection section 3 via, for example, interconnections not shown disposed in the stretchable substrate 6. It should be noted that the storage section 51 is not particularly limited, and there can be used, for example, a flash memory. Further, a communication method of the communication section 52 is not particularly limited, and either of wired communication and wireless communication can be used, but it is preferable to use the wireless communication such as Bluetooth (registered trademark). It should be noted that it is also possible for the functional section 5 to be provided with a biological acquisition section capable of obtaining biological information such as electrocardiographic information, myoelectric information, body temperature information, blood pressure information, and heartbeat information as needed besides the above.

As shown in FIG. 1, the coating section 10 covers the whole of the sensor 1. Thus, it is possible to protect the sensor 1 from an impact, dust, moisture, and so on, and it is possible to enhance the reliability of the sensor 1. Further, the coating section 10 has a stretching property equivalent to or higher than that of, for example, the stretchable substrate 6 so as not to hinder the extension and contraction of the stretchable substrate 6. The constituent material of such a coating section 10 is not particularly limited, and there can be used, for example, a variety of types of thermoplastic elastomer such as polyurethane elastomer, styrene thermoplastic elastomer, olefinic thermoplastic elastomer, vinyl chloride thermoplastic elastomer, esters thermoplastic elastomer, amide thermoplastic elastomer, silicone thermoplastic elastomer, and fluorinated thermoplastic elastomer, and a variety of rubber materials such as acrylic rubber, silicone rubber, butadiene rubber, and styrene rubber.

Further, on the surface of the coating section 10, there is disposed an adhesive layer not shown, and it is arranged that the sensor 1 can be mounted on the human H using the adhesive layer. It should be noted that the mounting method of the sensor 1 is not particularly limited, but it is possible to mount the sensor 1 on the human H using, for example, a band (a belt).

The sensor device 1 is described hereinabove. As described above, such a sensor 1 has the stretchable substrate 6 having a stretching property and the wires 7 provided to the stretchable substrate 6, wherein the wires 7 include the reference wire 71, and the sensing wires 72 larger in resistance value variation (change rate of the resistance) due to the extension and contraction of the stretchable substrate 6 than the reference wire 71. Thus, it is possible to detect the resistance value variation due to the factor other than the extension and contraction of the wires 7 using the reference wire 71. Therefore, by correcting the resistance values of the sensing wires 72 based on the resistance value of the reference wire 71, it is possible to obtain the resistance value variation due to the extension and contraction of the sensing wires 72. Further, it is possible to accurately detect the extension and contraction of the stretchable substrate 6 based on the resistance value variation due to the extension and contraction of the sensing wires 72. Therefore, it is possible to obtain the sensor 1 capable of detecting the resistance value variation due to the extension and contraction of the wires 7 with high accuracy.

Further, as described above, the sensor 1 has the motion detection section 3 (the detection section) for correcting the resistance values of the sensing wires 72 in accordance with the resistance value of the reference wire 71, and detecting the extension and contraction of the stretchable substrate 6 based on the resistance values of the sensing wires 72 thus corrected. Therefore, it is possible to detect the extension and contraction of the stretchable substrate 6 in the sensor 1 without outputting the resistance values of the reference wire 71 and the sensing wires 72 to the outside. Therefore, the sensor 1 high in convenience is obtained.

Further, as described above, the motion detection section 3 has the function of detecting the deterioration of the wires 7 in accordance with the resistance value of the reference wire 71. Thus, it is possible for the sensor 1 to prompt the user to replace the sensor 1 itself, to replace or repair the wires 7, and so on. Therefore, it is prevented that the sensor 1 degraded in detection accuracy continues to be used, and thus higher reliability can be exerted.

Further, as described above, in the sensor 1, the variation in the wiring length of the reference wire 71 with respect to the extension and contraction of the stretchable substrate 6 is smaller than the variation in the wiring length of the sensing wires 72. Thus, it is possible to suppress the resistance value variation due to the extension and contraction of the stretchable substrate 6 of the reference wire 71 to a low level. Therefore, it is possible to accurately detect the resistance value variation due to the factor other than the extension and contraction of the stretchable substrate 6 based on the resistance value of the reference wire 71. In particular, in the present embodiment, the wiring length of the reference wire 71 does not change even if the stretchable substrate 6 extends or contracts. Therefore, the advantage described above becomes more conspicuous.

Further, as described above, in the sensor 1, the reference wire 71 extends or contracts together with the stretchable substrate 6 with the shape deformation, while the sensing wires 72 extend or contract together with the stretchable substrate 6 with the elastic deformation. Thus, it is possible to detect the resistance value variation due to the factor other than the extension and contraction of the stretchable substrate 6 using the reference wire 71. Therefore, by correcting the resistance values of the sensing wires 72 based on the resistance value of the reference wire 71, it is possible to detect the resistance value variation due to the extension and contraction of the stretchable substrate 6 from the sensing wires 72. Therefore, the extension and contraction of the stretchable substrate 6 can be detected with higher accuracy.

Further, as described above, in the sensor 1, the reference wire 71 and the sensing wires 72 are formed of the same material. Thus, the variations of the reference wire 71 and the sensing wires 72 in resistance value due to the factors other than the extension and contraction of the stretchable substrate 6 can be made equal to each other. Therefore, the resistance values of the sensing wires 72 can more accurately be corrected based on the resistance value of the reference wire 71.

Further, as described above, in the sensor 1, the reference wire 71 and the sensing wires 72 are disposed side by side, and the separation distance D between the both end parts of the reference wire 71 and the separation distance D between the both end parts of the sensing wires 72 are equal to each other. Thus, the variation of the separation distance D in the case in which the stretchable substrate 6 extends or contracts can be made equal between the reference wire 71 and the sensing wires 72. Therefore, the influence of the extension and contraction of the stretchable substrate 6 becomes equal between the reference wire 71 and the sensing wires 72, and it is possible to suppress the dissociation of the deterioration degree between the reference wire 71 and the sensing wires 72 due to, for example, the repetitive extension and contraction. Therefore, it is possible to maintain the detection accuracy at a high level for a long period of time.

Further, as described above, in the sensor 1, the wires 7 include the plurality of sensing wires 72 different from each other in the resistance value variation (the change rate of the resistance) with respect to the extension and contraction of the stretchable substrate 6. Thus, the extension and contraction of the stretchable substrate 6 can be detected based on the resistance value variations of the plurality of sensing wires 72, and therefore, the extension and contraction of the stretchable substrate 6 can accurately be detected compared to the case in which, for example, the number of the sensing wires 72 is one. In particular, in the present embodiment, the extension and contraction of the stretchable substrate 6 are detected using the three sensing wires 72, and therefore, the advantage described above becomes more conspicuous. Further, for example, in the case in which the resistance value variation of the first sensing wire 73 has become larger than that of the second sensing wire 74, an abnormality of the wires 7 is assumed, and thus, an abnormality of the sensor 1 can be detected. Therefore, the reliability of the sensor 1 is improved.

Further, as described above, the sensing wires 72 (the first, second, and third sensing wires 73, 74, 75) are different in length (the wiring length) from each other. Thus, the resistance value variations of the sensing wires 72 with respect to the extension and contraction of the stretchable substrate 6 can be made different from each other with a simple configuration.

Second Embodiment

Figure 5:
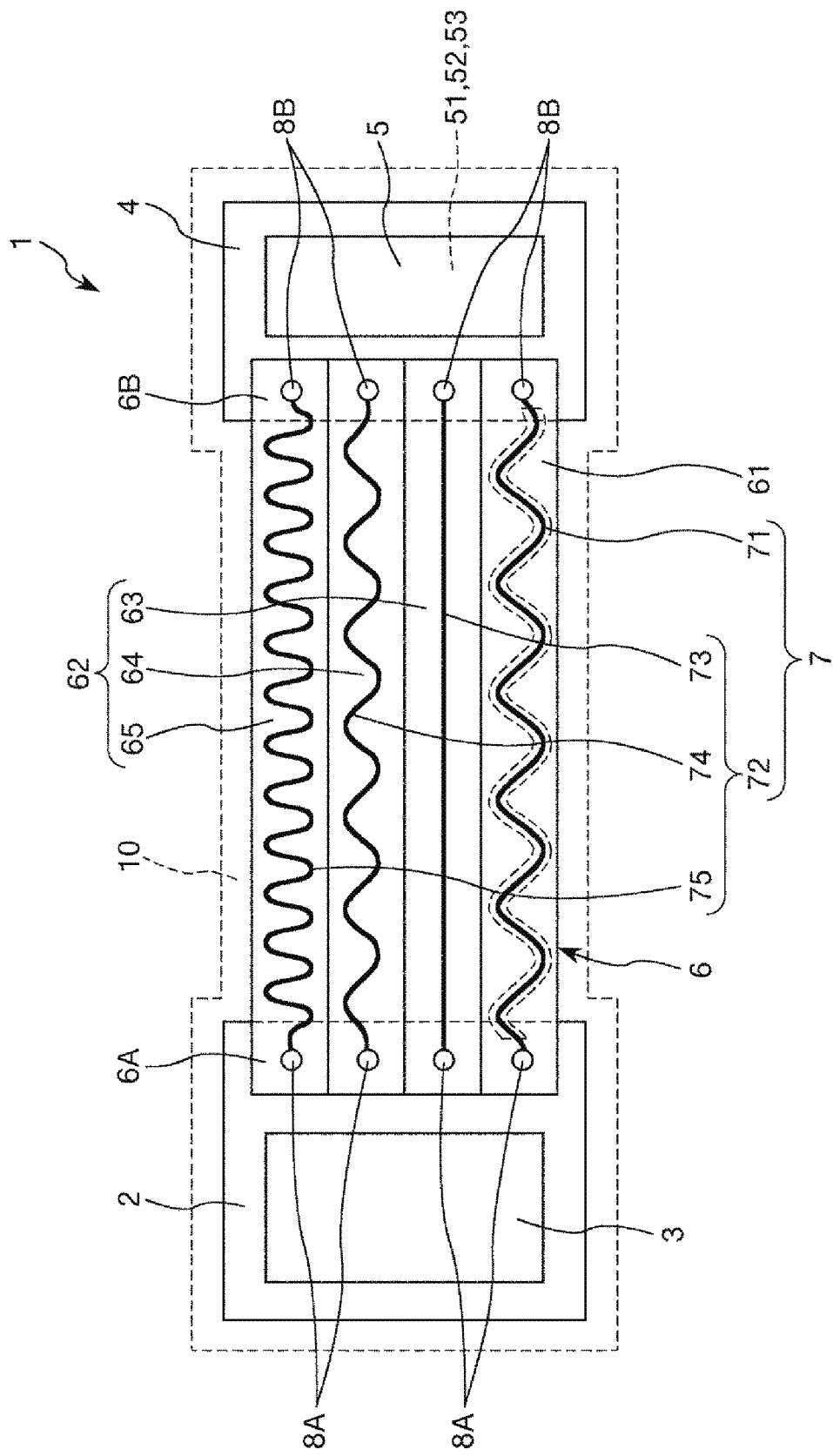
FIG. 5 is a plan view showing a sensor according to a second embodiment of the invention.

FIG. 5 is a plan view showing a sensor according to a second embodiment of the invention.

The sensor according to the present embodiment is substantially the same as the first embodiment described above except the point that the configuration of the stretchable substrate 6 is different.

It should be noted that in the following description, the present embodiment will be described with a focus on the difference from the first embodiment described above, and the description of substantially the same issues will be omitted. Further, in FIG. 5, the constituents substantially identical to those of the embodiment described above are denoted by the same reference symbols.

As shown in FIG. 5, in the sensor 1 according to the present embodiment, the stretchable substrate 6 has a reference wire support section 61 for supporting the reference wire 71, and sensing wire support sections 62 for supporting the respective sensing wires 72. Further, the sensing wire support sections 62 include a first sensing wire support section 63 for supporting the first sensing wire 73, a second sensing wire support section 64 for supporting the second sensing wire 74, and a third sensing wire support section 65 for supporting the third sensing wire 75. Further, the reference wire support section 61, the first sensing wire support section 63, the second sensing wire support section 64, and the third sensing wire support section 65 are respectively formed as separated members. In other words, in the first embodiment described above, the reference wire support section 61, the first sensing wire support section 63, the second sensing wire support section 64 and the third sensing wire support section 65 are formed integrally. According to such a configuration of the present embodiment, since the four wires 71, 73, 74, 75 are supported by the respective support sections different from each other, these wires 71, 73, 74, 75 can be replaced one by one. Therefore, the maintainability is enhanced compared to, for example, the configuration of the first embodiment described above. It should be noted that it is preferable for the first sensing wire support section 63, the second sensing wire support section 64 and the third sensing wire support section 65 to be the same in dimensions, constituent material, and stretching ratio, but this is not a limitation, and at least one of these conditions can be different therebetween.

According also to such a second embodiment as described above, substantially the same advantages as in the first embodiment described above can be exerted.

Third Embodiment

Figure 6:
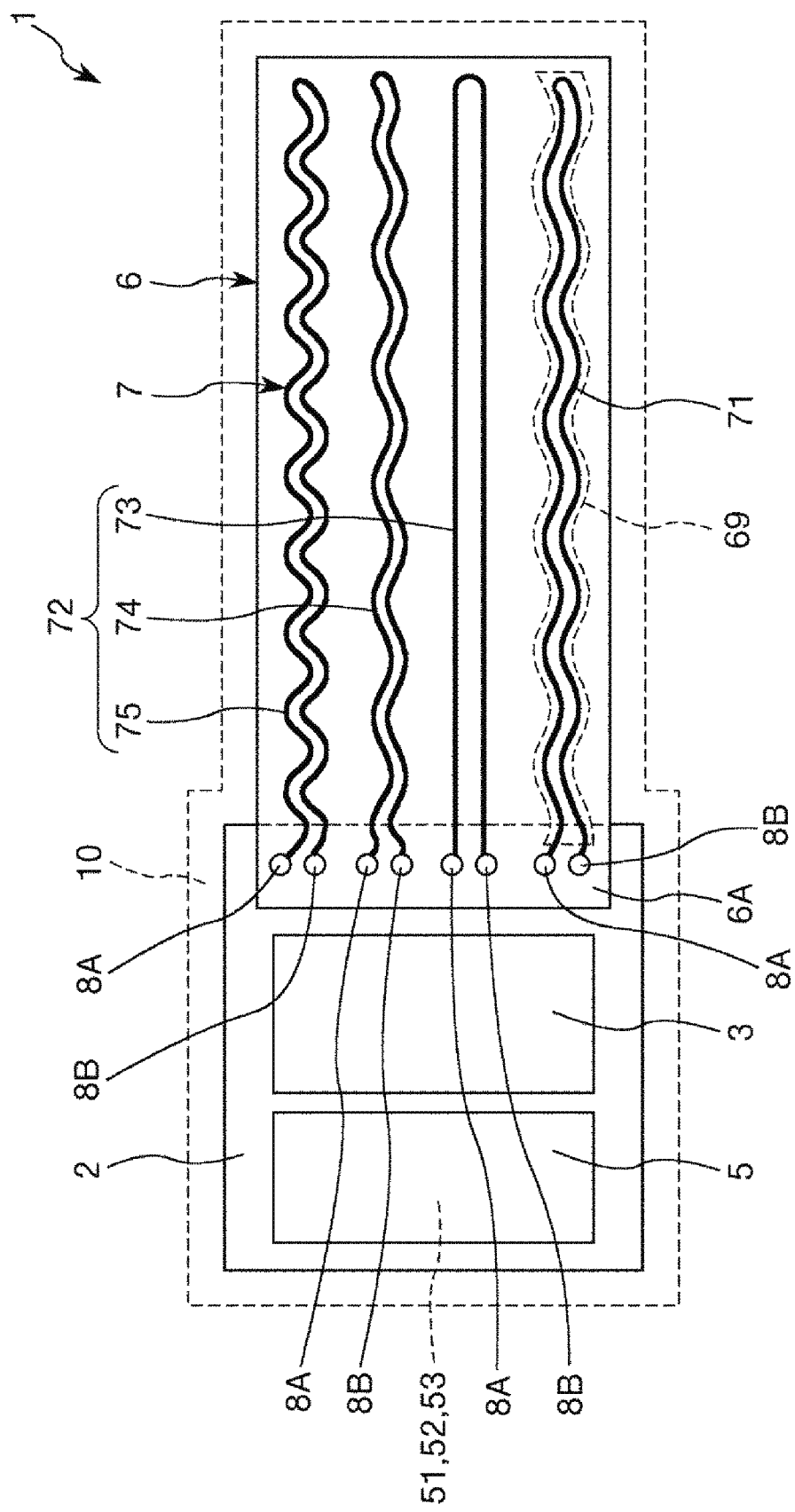
FIG. 6 is a plan view showing a sensor according to a third embodiment of the invention.

FIG. 6 is a plan view showing a sensor according to a third embodiment of the invention.

The sensor according to the present embodiment is substantially the same as the first embodiment described above except the point that the second substrate is omitted, and the point that the configuration of the wires 7 is different.

It should be noted that in the following description, the present embodiment will be described with a focus on the difference from the first embodiment described above, and the description of substantially the same issues will be omitted. Further, in FIG. 6, the constituents substantially identical to those of the embodiment described above are denoted by the same reference symbols.

As shown in FIG. 6, in the sensor 1 according to the present embodiment, the second substrate 4 is omitted from the configuration of the first embodiment described above, and the functional section 5 provided to the second substrate 4 is provided to the first substrate 2. By omitting the second substrate 4 from the first embodiment described above in such a manner, miniaturization of the sensor 1 can be achieve compared to the first embodiment.

Further, the terminals 8A, 8B of the both end parts of each of the reference wire 71, the first sensing wire 73, the second sensing wire 74, and the third sensing wire 75 are located in the first fixation section 6A, and the reference wire 71, the first sensing wire 73, the second sensing wire 74, and the third sensing wire 75 are each folded back at an end part of the stretchable substrate 6 to be disposed so as to reciprocate in the extending direction of the stretchable substrate 6 to have a U-shape. Thus, the wiring length of each of the first sensing wire 73, the second sensing wire 74, and the third sensing wire 75 can roughly be doubled compared to, for example, the configuration of the first embodiment described above. Therefore, the resistance value variations of the first sensing wire 73, the second sensing wire 74, and the third sensing wire 75 due to the extension and contraction of the stretchable substrate 6 can be made larger, and thus, the extension and contraction of the stretchable substrate 6 can more accurately be detected.

According also to such a third embodiment as described above, substantially the same advantages as in the first embodiment described above can be exerted. It should be noted that it is possible to adopt a configuration in which, for example, a part from the start point to a middle point of each of the wires 71, 73, 74, 75 is disposed on one surface of the stretchable substrate 6, and a part from the middle point to the end point thereof is disposed on the other surface thereof. Thus, the contact (short circuit) between the former part and the latter part can more surely be prevented.

Fourth Embodiment

Figure 7:
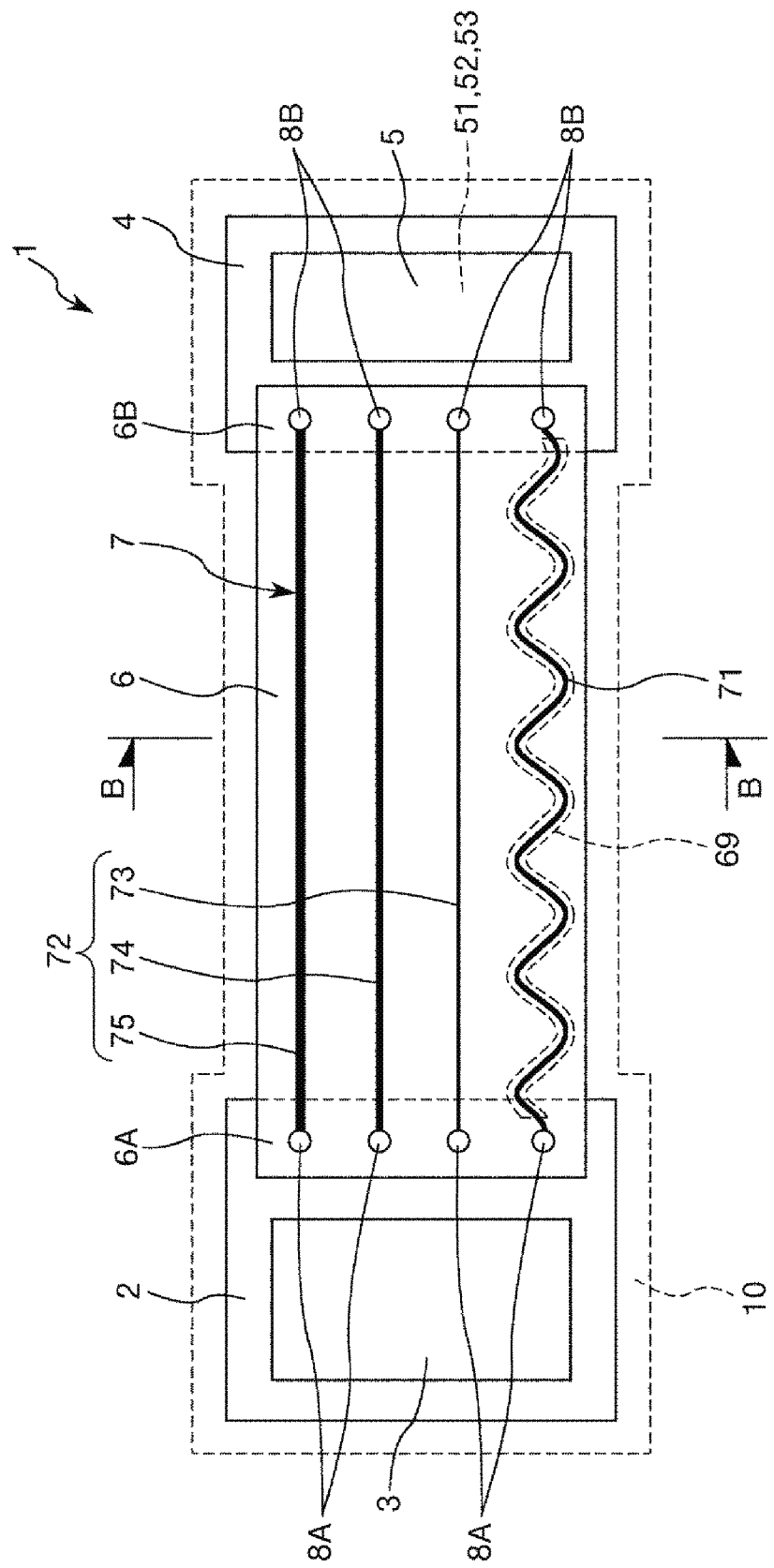
FIG. 7 is a plan view showing a sensor according to a fourth embodiment of the invention.
Figure 8:
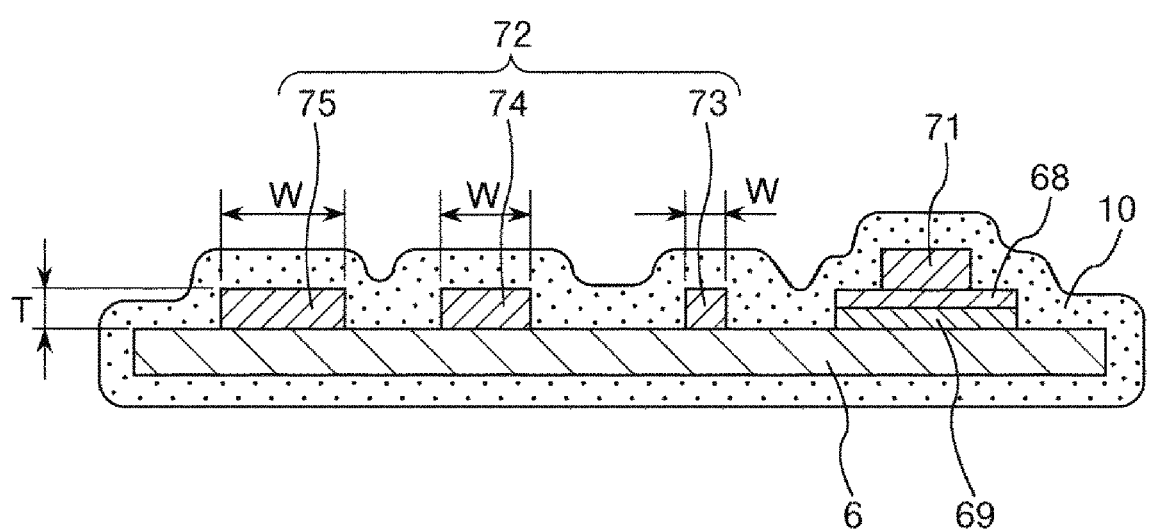
FIG. 8 is a cross-sectional view along the line B-B in FIG. 7.

FIG. 7 is a plan view showing a sensor according to a fourth embodiment of the invention. FIG. 8 is a cross-sectional view along the line B-B in FIG. 7.

The sensor according to the present embodiment is substantially the same as the first embodiment described above except the point that the configuration of the sensing wires 72 is different.

It should be noted that in the following description, the present embodiment will be described with a focus on the difference from the first embodiment described above, and the description of substantially the same issues will be omitted. Further, in FIG. 7 and FIG. 8, the constituents substantially identical to those of the embodiment described above are denoted by the same reference symbols.

As shown in FIG. 7, in the sensor 1 according to the present embodiment, the first sensing wire 73, the second sensing wire 74, and the third sensing wire 75 each have a linear shape, and have wiring lengths roughly equal to each other. Further, the first sensing wire 73, the second sensing wire 74, and the third sensing wire 75 are different in cross-sectional area from each other. Specifically, as shown in FIG. 8, the second sensing wire 74 is larger in width W than the first sensing wire 73, and is therefore smaller in the resistance value variation due to the extension and contraction of the stretchable substrate 6 than the first sensing wire 73. Further, the third sensing wire 75 is larger in width W than the second sensing wire 74, and is therefore smaller in the resistance value variation due to the extension and contraction of the stretchable substrate 6 than the second sensing wire 74.

As described above, in the present embodiment, the sensing wires 72 (the first, second, and third sensing wires 73, 74, 75) are different in cross-sectional area (the width W) from each other. Thus, the resistance value variations of the sensing wires 72 with respect to the extension and contraction of the stretchable substrate 6 can be made different from each other with a simple configuration. In particular, since the first, second, and third sensing wires 73, 74, 75 each have a linear shape, the space for disposing the first, second, and third sensing wires 73, 74, 75 can be reduced compared to the first embodiment described above, and it is possible to achieve reduction in size of the sensor 1.

According also to such a fourth embodiment as described above, substantially the same advantages as in the first embodiment described above can be exerted.

Fifth Embodiment

Figure 9:
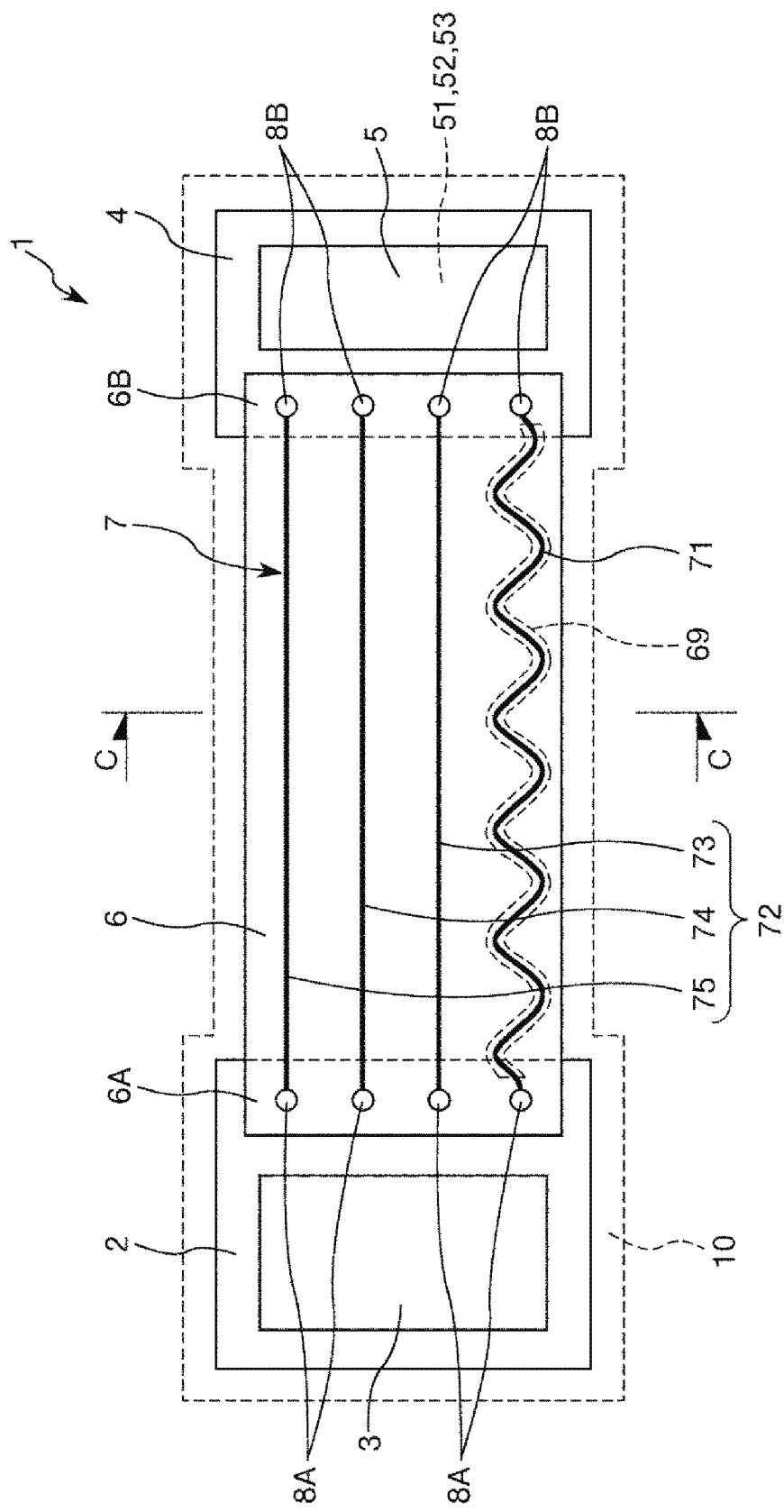
FIG. 9 is a plan view showing a sensor according to a fifth embodiment of the invention.
Figure 10:
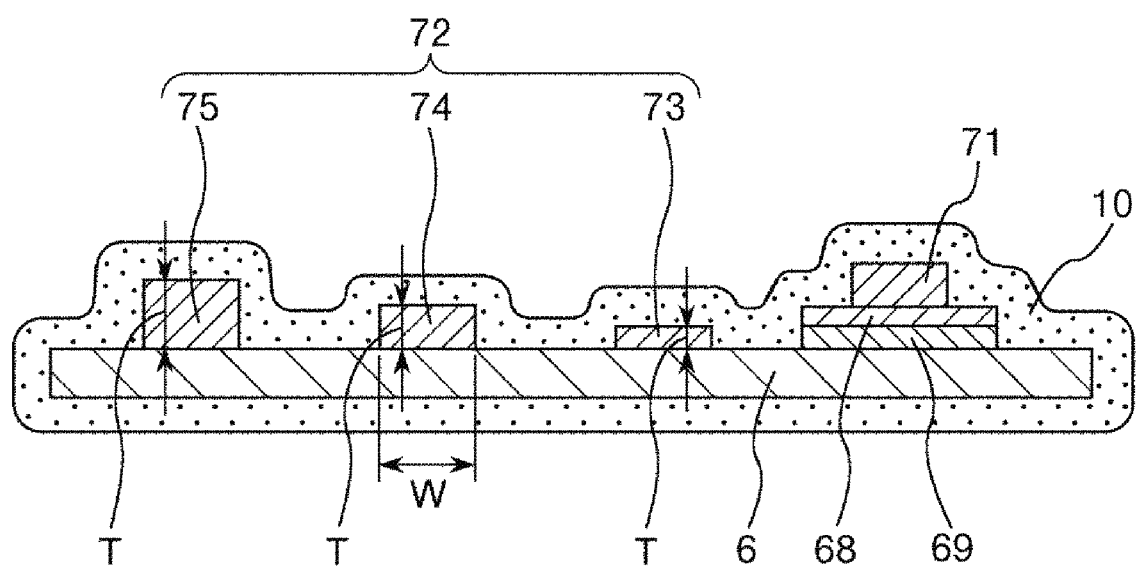
FIG. 10 is a cross-sectional view along the line C-C in FIG. 9.

FIG. 9 is a plan view showing a sensor according to a fifth embodiment of the invention. FIG. 10 is a cross-sectional view along the line C-C in FIG. 9.

The sensor according to the present embodiment is substantially the same as the first embodiment described above except the point that the configuration of the sensing wires 72 is different.

It should be noted that in the following description, the present embodiment will be described with a focus on the difference from the first embodiment described above, and the description of substantially the same issues will be omitted. Further, in FIG. 9 and FIG. 10, the constituents substantially identical to those of the embodiment described above are denoted by the same reference symbols.

As shown in FIG. 9, in the sensor 1 according to the present embodiment, the first sensing wire 73, the second sensing wire 74, and the third sensing wire 75 each have a linear shape, and have wiring lengths roughly equal to each other. Further, the first sensing wire 73, the second sensing wire 74, and the third sensing wire 75 are different in cross-sectional area from each other. Specifically, as shown in FIG. 10, the second sensing wire 74 is larger in thickness T than the first sensing wire 73, and is therefore smaller in the resistance value variation due to the extension and contraction of the stretchable substrate 6 than the first sensing wire 73. Further, the third sensing wire 75 is larger in thickness T than the second sensing wire 74, and is therefore smaller in the resistance value variation due to the extension and contraction of the stretchable substrate 6 than the second sensing wire 74.

As described above, in the present embodiment, the sensing wires 72 (the first, second, and third sensing wires 73, 74, 75) are different in cross-sectional area (the thickness T) from each other. Thus, the resistance value variations of the sensing wires 72 with respect to the extension and contraction of the stretchable substrate 6 can be made different from each other with a simple configuration. In particular, since the first, second, and third sensing wires 73, 74, 75 each have a linear shape, the space for disposing the first, second, and third sensing wires 73, 74, 75 can be reduced compared to the first embodiment described above, and it is possible to achieve reduction in size of the sensor 1.

According also to such a fifth embodiment as described above, substantially the same advantages as in the first embodiment described above can be exerted.

Although the sensor according to the invention is described hereinabove based on the embodiments shown in the accompanying drawings, the invention is not limited to these embodiments, but the configuration of each of the components can be replaced with one having an identical function and an arbitrary configuration. Further, it is also possible to add any other constituents to the invention. Further, it is also possible to arbitrarily combine any of the embodiments with each other. For example, the sensing wires can also be different in both of the wiring length and the cross-sectional area from each other.

The entire disclosure of Japanese Patent Application No. 2017-069353 filed on Mar. 30, 2017 is expressly incorporated by reference herein.

What is claimed is:

1. A sensor comprising:
a stretchable substrate having a stretching property;
a plurality of wires provided to the stretchable substrate, the plurality of wires including a first wire and a second wire; and
a restriction member provided to the stretchable substrate along the first wire,
wherein the second wire is larger in resistance value variation due to extension of the stretchable substrate than the first wire,
the restriction member is configured to extend and contract together with the stretchable substrate with shape deformation,
the first wire extends and contracts together with the stretchable substrate with the shape deformation and without substantial elastic deformation due to the extension and contraction of the restriction member, and
the second wire extends and contracts together with the stretchable substrate with elastic deformation.

2. The sensor according to claim 1, further comprising:
a detection section adapted to correct a resistance value of the second wire in accordance with a resistance value of the first wire, and detect the extension and contraction of the stretchable substrate based on the resistance value of the second wire which has been corrected.

3. The sensor according to claim 2, wherein
the detection section detects deterioration of the plurality of wires in accordance with the resistance value of the first wire.

4. The sensor according to claim 1, wherein
a variation in wiring length of the first wire with respect to the extension of the stretchable substrate is smaller than a variation in wiring length of the second wire.

5. The sensor according to claim 1, wherein
the first wire and the second wire are formed of a same material.

6. The sensor according to claim 1, wherein
the first wire and the second wire are disposed side by side, and
a separation distance between both end parts of the first wire and a separation distance between both end parts of the second wire are equal to each other.

7. The sensor according to claim 1, wherein
the plurality of wires includes a plurality of the second wires different in change rate of resistance with respect to the extension of the stretchable substrate from each other.

8. The sensor according to claim 7, wherein
the second wires are different in length from each other.

9. The sensor according to claim 7, wherein
the second wires are different in cross-sectional area from each other.

* * * * *